US00PP21888P2

(12) United States Plant Patent
Korlipara

(10) Patent No.: US PP21,888 P2
(45) Date of Patent: Apr. 26, 2011

(54) *ECHINACEA* PLANT NAMED 'CORAL REEF'

(50) Latin Name: ***Echinacea* spp.**
Varietal Denomination: Coral Reef

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 12/655,572

(22) Filed: Dec. 31, 2009

(51) Int. Cl.
*A01H 5/00* (2006.01)

(52) U.S. Cl. ..... Plt./428

(58) Field of Classification Search ..... Plt./263, Plt./428

See application file for complete search history.

*Primary Examiner* — Susan B McCormick Ewoldt

(74) *Attorney, Agent, or Firm* — Klarquist Sparkman, LLP

(57) ABSTRACT

A new and distinct *Echinacea* plant named 'Coral Reef' characterized by medium large, dark orange to coral ray florets, enlarged coral red disc florets forming an anemone-type inflorescence, well-branched flower stalks, and excellent vigor.

1 Drawing Sheet

Botanical denomination: *Echinacea* spp.
Variety designation: 'Coral Reef'.

The present invention relates to a new and distinct cultivar of *Echinacea* and given the cultivar name 'Coral Reef'. *Echinacea* is in the family Asteraceae. This new cultivar originated from a planned breeding program using *Echinacea purpurea* 'Razzmatazz' (U.S. Plant Pat. No. 13,894) as the seed parent and unnamed proprietary, unreleased plant from a third generation hybrid of *Echinacea* (*paradoxa*×*purpurea* 'Ruby Giant'), for the pollen parent. The exact pollen parent of this selection is unknown.

Compared to *Echinacea purpurea* 'Razzmatazz' (U.S. Plant Pat. No. 13,894), the seed parent, the new variety has orange to coral rather than dark pink flowers.

Compared to the pollen parent, *Echinacea* (*paradoxa*× *purpurea* 'Ruby Giant'), the new variety has coral rather than rose pink flowers and anemone-type inflorescence rather the "single" type with normal disc florets.

Compared to *Echinacea* 'Hot Papaya' (U.S. Plant Pat. No. 21,022), the new variety has larger flowers, ray florets that don't strongly reflex, and different overall orange coral color.

This new *Echinacea* cultivar is distinguished by:

1. large, dark orange to coral ray florets
2. enlarged coral red disc florets forming an anemone-type, semi-double inflorescence
3. well-branched flower stalks; and
4. excellent vigor This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a group of flowers of *Echinacea* 'Coral Reef' on a plant growing in full sun in the summer in Canby, Oreg.

FIG. 2 shows the whole plant.

FIG. 3 shows a close up of the flowers.

DETAILED PLANT DESCRIPTION

The following is a detailed description of the new *Echinacea* cultivar based on observations of a 9-months-old specimen growing in the ground in the field in full sun under typical outdoor conditions in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on The Royal Horticultural Society Colour Chart.

Plant:

*Type.*—Herbaceous perennial.
*Hardiness.*—USDA Zones 4 to 9.
*Size.*—50 cm wide and from 69 cm to 90 cm tall to top of flowers.
*Form.*—Basal clump.
*Vigor.*—Excellent.
*Roots.*—Fibrous, with many downward growing and few laterals, ivory in color, Yellow White 158D, roots develop easily from cuttings from the crown.

Stem (flowering):

*Type.*—Ascending, with 7 flowering branches on main stems.
*Size.*—Branching to 87 cm tall to a terminal flower and 11 mm wide at base.
*Internode length.*—3 cm to 8 cm.
*Surface texture.*—Strigose.
*Color.*—Yellow Green 146B mottled with Brown 200A.

Leaf (basal):

*Type.*—Simple.
*Shape.*—Lanceolate to broadly lanceolate.
*Arrangement.*—Basal.
*Blade size.*—Grows to 21 cm long and 8 cm wide.
*Margins.*—Entire.
*Apex.*—Acute to acuminate.
*Base.*—Attenuate.
*Surface texture.*—Strigose on both sides.

*Venation.*—Pinnate, with 5 main veins from the base.

*Color.*—Topside, Yellow Green 147A, bottom side closest to Yellow Green 147B.

*Petiole description.*—Grows to 16 cm long and 6 mm wide (at base), glabrous, Yellow Green 146D except topside inside petiole furrow and bottom ¼ where Greyed Purple 187A.

Leaf (stem):

*Type.*—Simple.

*Shape.*—Lanceolate.

*Arrangement.*—Alternate.

*Blade size.*—Grows to 18 cm long and 4 cm wide.

*Margins.*—Entire.

*Apex.*—Acute.

*Base.*—Attenuate.

*Surface texture.*—Strigose on both sides.

*Venation.*—Pinnate, with 5 main veins from the base.

*Color.*—Topside, Yellow Green 147A; bottom side between Yellow Green 147A and Yellow Green 147B.

*Petiole description.*—On lowermost leaves, clasping, grows to 4 cm long and 5 mm wide above the clasp, strigose, Yellow Green 147B.

Inflorescence:

*Type.*—Composite on terminal stalked heads.

*Number of flowering stems from the ground.*—3 to 8.

*Flowering stem.*—Grows to 87 cm tall from the base of the plant to the terminal flower and can grow to 29 cm long from the top stem leaf to the base of a flower head; branched, about 12 flowers per stem; diameter growing to 10 mm wide near the flower head; strigose, Yellow Green 146B mottled with Brown 200A.

*Size.*—Grows to 10.5 cm wide and 4.5 cm deep as disc enlarges.

*Form.*—Ray petals held horizontally, mature disc is conic.

*Immature inflorescence.*—Grows to 2.7 cm wide and 2.4 cm deep, ray florets held upright and rolled up so only the back color shows, Yellow Green 150C tinted Greyed Red 178A, disc background is Yellow Green 145A, foreground is Greyed Purple 187B.

*Ray florets.*—Without pistil or stamen, 22 to 27 in number, grows to 42 mm long and 10 mm wide, oblanceolate with the tip two toothed (each acute), entire margins, base attenuate, glabrous on both sides; topside color of young mature ray florets Greyed Orange 169A overall with the top ⅓ slightly lighter, Greyed Orange 170A, and the base Greyed Purple 187B; older florets lighten to Greyed Red 180C and 180B, bottom side closest to Greyed Purple 186B.

*Disc.*—Flat becoming conic, becoming 30 mm deep and 65 mm wide with maturity, overall color Red 47B.

*Disc florets.*—About 350 in number, grow to 22 mm long and 2 mm to 8 mm wide, each with one persistent, very stiff bract (12 mm long and the top 3 mm with Greyed Purple 187A on tip then Orange Red 32A, rest Yellow Green 148D); showy corollas to 22 mm long and 2 to 10 mm wide depending on whether mostly tubular with 5 lobes or tubular on the bottom only with the lobes spreading out like a fan, glabrous, outside color Greyed Purple 186B, showy inside color Red 47A lightening with age to Greyed Orange 170A with Greyed Purple 187B on the lobe tips; pistil 8 mm long, ovary 2.3 mm long, White 155A, style 4 mm long White 155A, 2-branched stigma spreading 1.2 mm wide, tinted Greyed Purple 187B; stamen 4 in number, 3 mm long, anthers 1.5 mm long and Black 202A, filaments 1.5 mm long, White 155A, no pollen, male sterile.

*Phyllaries.*—In 4 leafy series, area 3.5 cm wide and 10 mm deep, lobes lanceolate in shape, held horizontally, grow to 17 mm long and 4.5 mm wide, Yellow Green 147B, margins strigose, tip acute, strigose on both sides.

*Receptacle.*—Grows to 14 mm wide and 12 mm deep, White 155A.

*Bloom period.*—July through October in Canby, Oreg.

*Fragrance.*—Light, floral.

*Lastingness.*—Each inflorescence lasts about two weeks in Canby, Oreg.

*Seeds.*—0 to 1 per inflorescence, each 3 mm long and 2.5 mm wide, oval, Brown 200C.

*Fertility.*—Poor.

Disease and pests: *Echinacea* are susceptible to leaf miners, powdery mildew, bacterial spots, and gray mold. None of these have been observed on plants grown under commercial conditions in Canby, Oreg. No resistance is known.

I claim:

1. A new and distinct *Echinacea* plant as herein illustrated and described.

* * * * *

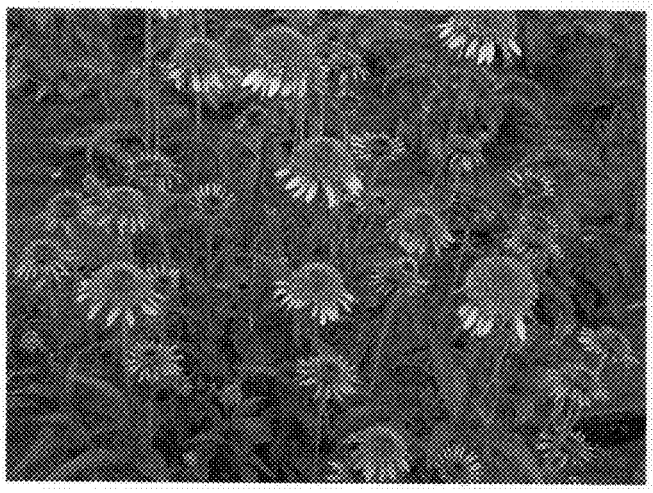
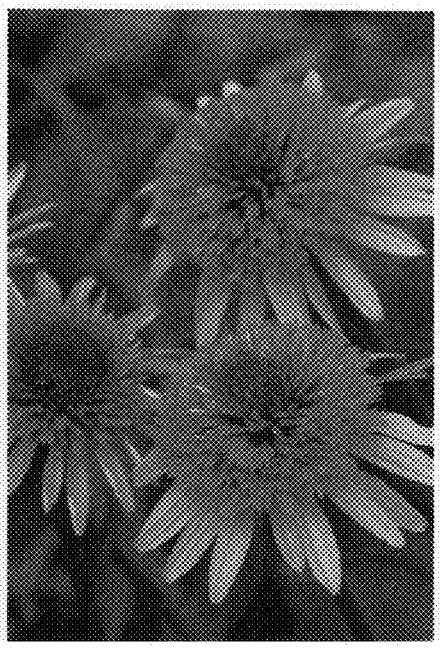

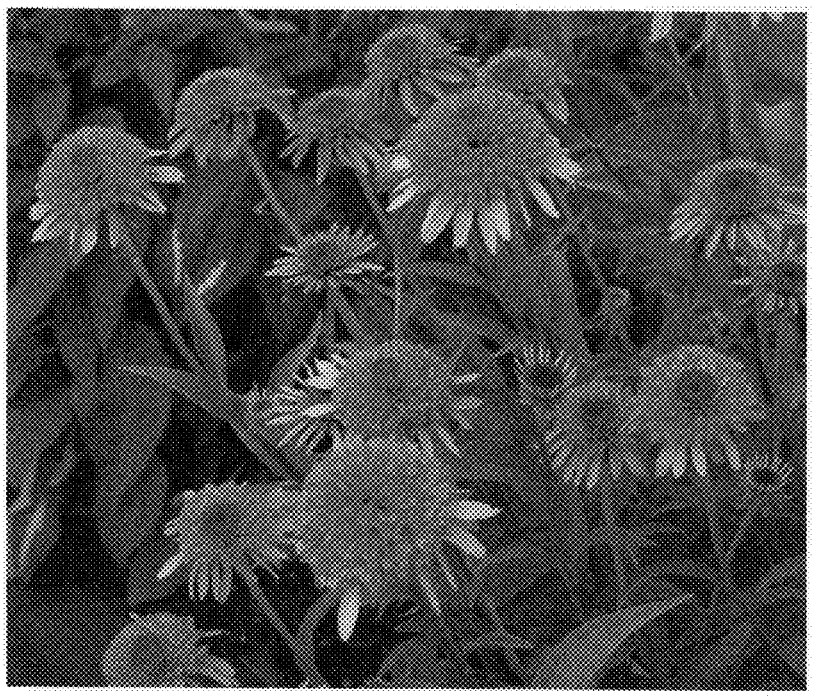
Figure 1 above, Figure 2 below left,
Figure 3 below, right